(12) United States Patent
Burdulis

(10) Patent No.: US 6,605,075 B1
(45) Date of Patent: Aug. 12, 2003

(54) FLUSHABLE HUB

(75) Inventor: Al Burdulis, San Francisco, CA (US)

(73) Assignee: Ethicon, Inc., Somerville, NJ (US)

( * ) Notice: Subject to any disclaimer, the term of this patent is extended or adjusted under 35 U.S.C. 154(b) by 0 days.

(21) Appl. No.: 09/469,741

(22) Filed: Dec. 21, 1999

(51) Int. Cl.[7] .................. A61M 25/16; A61M 25/18; A61M 39/00; A61M 39/10
(52) U.S. Cl. .................. 604/533; 604/264; 604/93.01; 604/500; 600/585
(58) Field of Search ................. 604/533, 523, 604/247, 246, 93.01, 19, 500, 506, 96.01, 160, 264; 600/585

(56) References Cited

U.S. PATENT DOCUMENTS

| | | | | |
|---|---|---|---|---|
| 3,707,972 A | * | 1/1973 | Villari et al. | 128/349 R |
| 4,291,691 A | * | 9/1981 | Cabal et al. | 128/204.18 |
| 4,508,533 A | * | 4/1985 | Abramson | 604/35 |
| 4,648,865 A | * | 3/1987 | Aigner | 604/4 |
| 4,953,547 A | * | 9/1990 | Poole, Jr. | 128/203.12 |
| 5,334,160 A | * | 8/1994 | Ellis | 604/167 |
| 5,357,961 A | * | 10/1994 | Fields et al. | 128/658 |
| 5,620,427 A | * | 4/1997 | Werschmidt et al. | 604/283 |
| 5,643,227 A | * | 7/1997 | Stevens | 604/264 |
| 5,658,309 A | * | 8/1997 | Berthiaume et al. | 606/192 |
| 5,766,211 A | * | 6/1998 | Wood et al. | 604/32 |
| 5,830,189 A | | 11/1998 | Chang | |
| 6,007,522 A | * | 12/1999 | Agro et al. | 604/264 |

\* cited by examiner

Primary Examiner—Brian L. Casler
Assistant Examiner—Jennifer Maynard
(74) Attorney, Agent, or Firm—Blakely, Sokoloff, Taylor & Zafman, LLP

(57) ABSTRACT

A catheter unit comprising a catheter having a hub, a connector and catheter, the connector comprising a first port, a second port, and third port. The first port, located at the proximal end of the connector and protruding from the connector, is coupled to a lock member. The second port, located within a cylindrical portion of the connector, is adapted to receive a guidewire. The third port is located at the distal end of the connector.

12 Claims, 4 Drawing Sheets

FLUSHABLE HUB

BACKGROUND OF THE INVENTION

1. Field of the Invention

The present invention relates generally to medical devices and more particularly to a connector such as a hub of a catheter.

2. Description of Related Art

Despite significant advances made in intravascular devices such as catheters, blood or other bodily fluids that collects in a flash chamber may escape from a catheter thereby potentially exposing a healthcare worker or another person to blood-borne pathogens. In view of the potential of healthcare workers contacting blood borne pathogens such as HIV and hepatitis, there exists a need to provide catheters that reduce this risk. Although existing devices are capable of reducing the risk that a person will contact blood-borne pathogens through inadvertent needle trauma, these prior devices or apparatus are not capable of being used with all types of catheters. Accordingly, there remains a need for the development of additional needle blunting devices and/or apparatus for preventing or reducing the risk of exposure to blood or other bodily fluids due to fluid escaping from the catheter.

Connectors for catheters are known in the art as shown by U.S. Pat. No. 5,357,961 issued to Fields. However, several disadvantages exist to using a Y-shaped connector or a L-shaped connector. First, these types of shapes of the connectors are bulky and may be caught in the dressing or clothing of a patient. If a catheter is caught on a dressing or some type of material, the catheter generally remains in its position while the patient moves. This results in discomfort to the patient. Second, the hub is bulky and is more difficult to handle by a health care worker. Third, conventional flushable hubs require more complex parts to be functional. For example, the leg of the L- shaped or Y-shaped hub causes the manufacturing process to be more complex. Fourth, the complexity of the process of manufacturing the L-shape and Y-shape connector is costly. Accordingly, it is desirable to produce a connector that addresses the problems associated with conventional connectors.

SUMMARY OF THE INVENTION

A catheter unit comprising a catheter having a hub and connector, the connector comprising a first port, a second port, and third port. The first port, located at the proximal end of the connector and protruding from the connector, is coupled to a lock member. The second port, located within a middle portion of the connector, is adapted to receive a guidewire. The third port is located at the distal end of the connector. Additional features, embodiments, and benefits will be evident in view of the figures and detailed description presented herein.

BRIEF DESCRIPTION OF THE DRAWINGS

The features, aspects, and advantages of the invention will become more thoroughly apparent from the following detailed description, appended claims, and accompanying drawings in which:

DETAILED DESCRIPTION OF THE INVENTION

The following detailed description and the accompanying drawings are provided for the purpose of describing and illustrating presently preferred embodiments of the invention only, and are not intended to limit the scope of the invention in any way.

Figure 1:
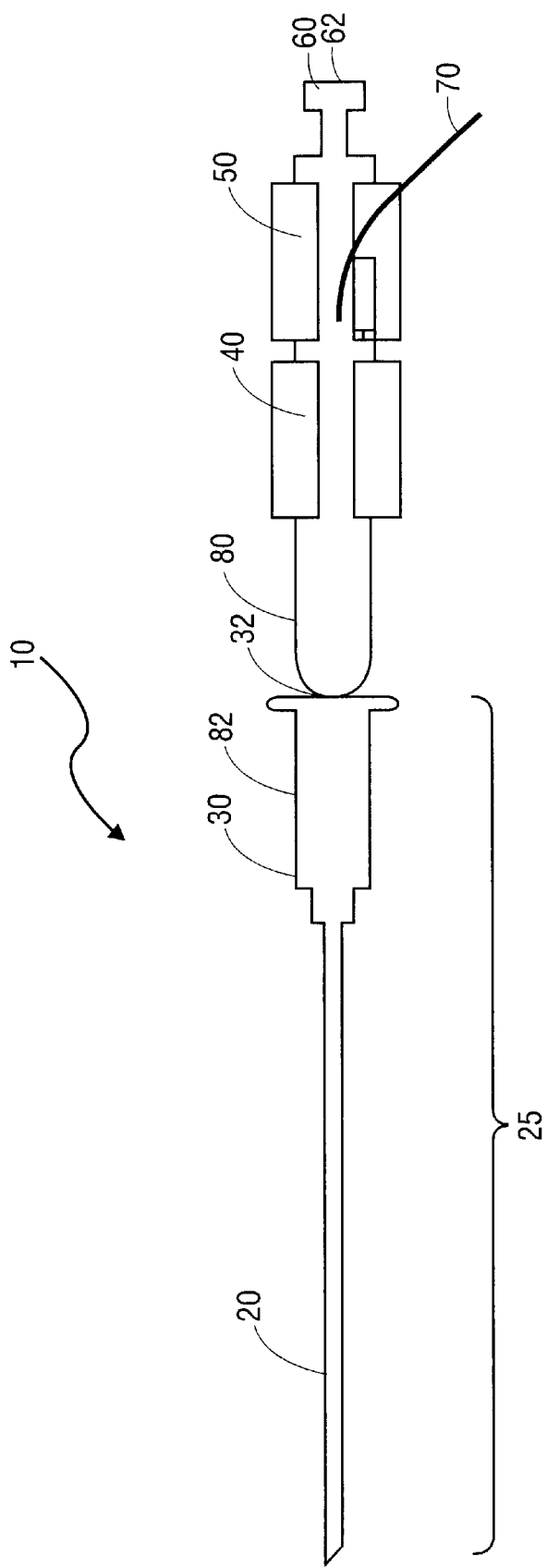
FIG. 1 is a side view of an embodiment of an intravascular assembly in accordance with the present invention.

With reference to one embodiment of the invention shown in FIG. 1, there is provided assembly 10 that may be used to facilitate percutaneous insertion of an intravascular cannula, tube, and catheter 20. Intravascular assemblies include a variety of catheters such as peripherally central catheters (PICC) that allow for repeated access to the patient's vascular or venous system. Intravascular assembly 10 comprises a catheter 20, an introducer assembly 30, a male leur 40, a wire sealed tube 50, a female leur lock 60, and a connector 80.

Figure 4:
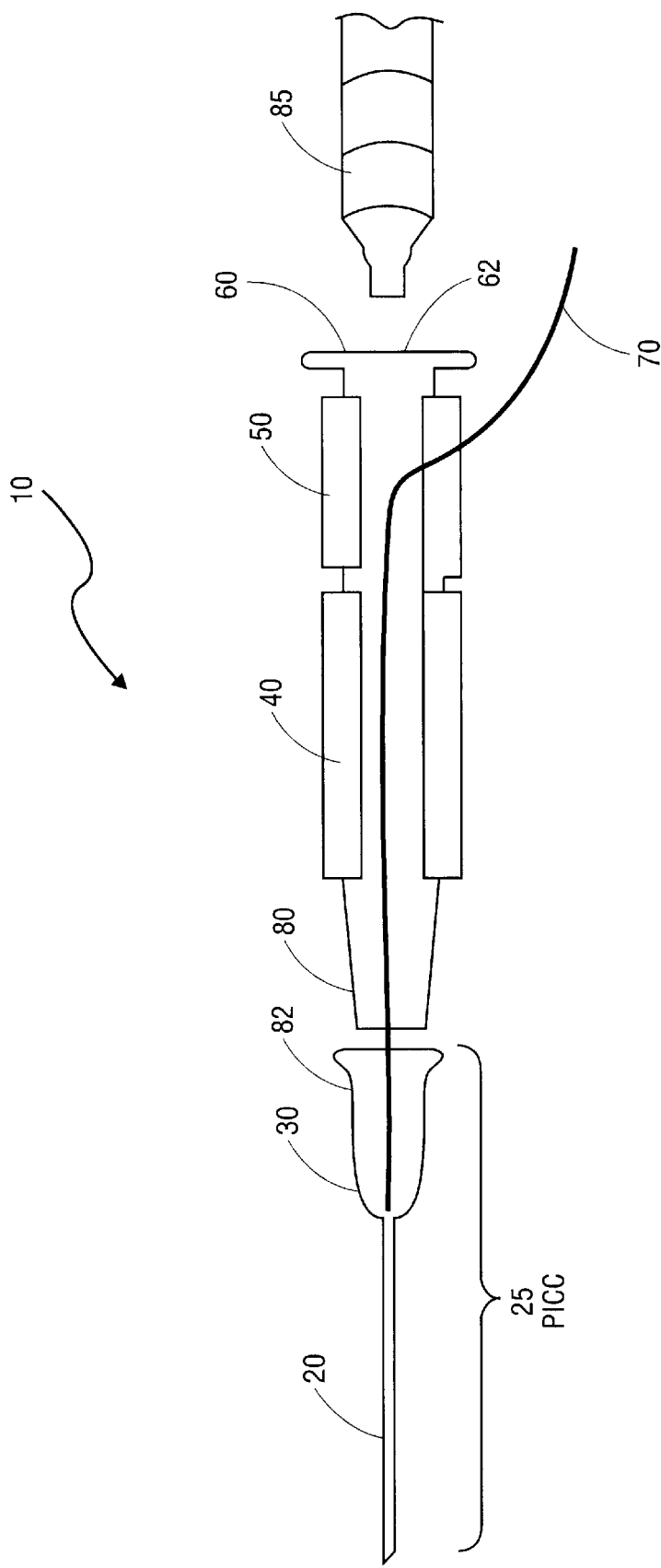
FIG. 4 is a side view of an embodiment of an intravascular assembly in accordance with the present invention.

PICC 25 comprises a hub 82 and catheter 20. Hub 82 and catheter 20 are fastened together to form a continuous and leakless assembly. Catheter 20 may be constructed of polyurethane, silicone rubber, or any other suitable material. PICC 25 is connected to a 3-way connector 80 by hub 82 sliding over the 3-way connector's outlet port 32. Hub 82 has appropriate dimensions allowing it to be securely fitted to outlet port 32. Outlet port 32 is in communication between the 3-way connector 80 and the proximal end of PICC 25. Connector 80 is also coupled to female leur lock 60 using conventional methods such as female leur lock 60 having a cylindrical portion that has an outer diameter smaller than the inner diameter of connector 80. Inlet port 62 of connector 80 is secured to syringe 85 for PICC 25 as shown in FIG. 4.

Figure 2:
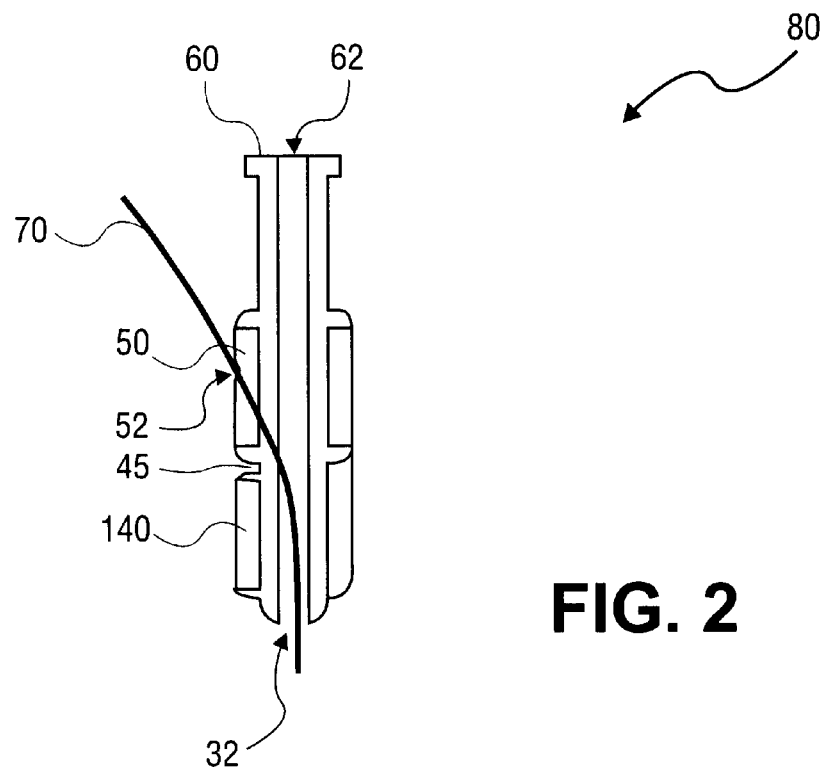
FIG. 2 is an enlarged sectional view of a hub in the present invention.
Figure 3:
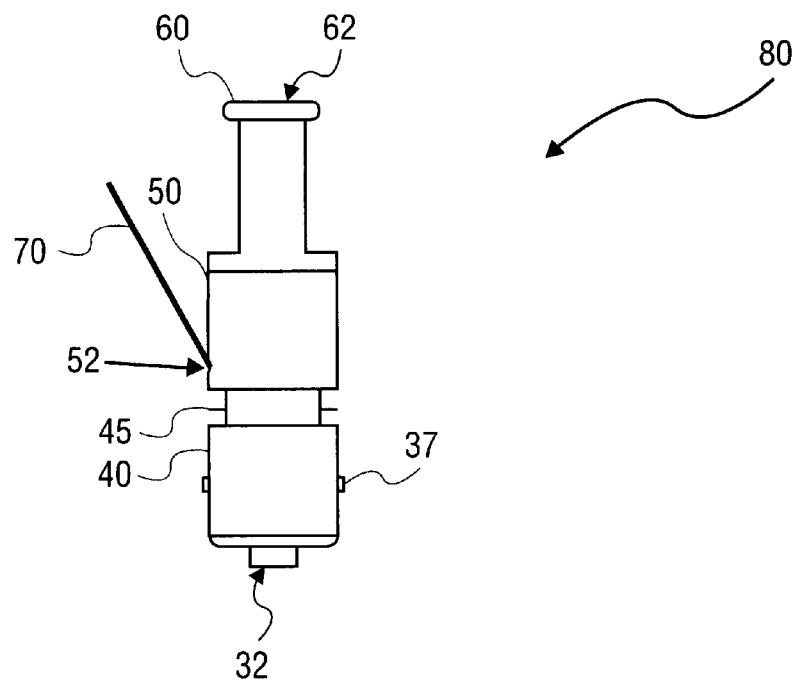
FIG. 3 is an enlarged view of the same hub as in FIG. 2.

As shown in FIGS. 2 and 3, connector 80 has three ports—a guidewire port 52 that is located on the side of connector 80, an inlet port 62, and an outlet port 32. All three ports are preferably integral to each other and form a cavity.

One advantage to having connector 80 configured without an L-shape or Y-shape is that the catheter is easier to use especially when the catheter is repetitively used as in a PICC. This is due to the ease of inserting the catheter into the patient without obstruction. Flushing the intravascular assembly while moving the catheter through a patient's body is made easier by a connector configured without an L-shape or Y-shape. Another advantage of the invention is that an intravascular assembly that uses the connector is more easily "site cleaned" by a health care worker. For example, when the hub is in use, the hub should be cleaned to minimize the risk of infection. The various embodiments of the invention, by using an inline design, is more easily cleaned than conventional flushable guide wire hubs because there is no Y-leg or L-leg off of the connector. Another advantage to the device is that there are fewer and less complicated parts to manufacture. Therefore, there is a reduced risk of quality defects in the part because of the less parts needed making the device generally easier to manufacture. This in turn reduces the cost of manufacturing the device. Another advantage relates to the ease of using the device compared to conventional devices. Accordingly, the risk of misusing the device by a health care worker is reduced. Note that variations to the connector may consist of any modification to any type of design that eliminated the L-leg or Y-leg to the connector.

Connector 80 and catheter 20 are fastened together to form a continuous and generally leak-proof assembly. Catheter 20 can be constructed of any suitable material, such as polyurethane, silicone rubber, or other suitable self sealing material.

To insert intravascular assembly 10 of FIG. 4 into a patient, guidewire 70 is run through the length of catheter 20. Guidewire 70 stiffens catheter 20 which allows the guidewire 70 to make its way through a patient's vascular system. Guidewire 70 comprises a hydrophilically coated stylet. Guidewire 70 may or may not have a handle at one end. However, it is preferred that guidewire 70 have a handle to make it easier to grip guidewire 70 while inserting catheter 20 through guidewire 70.

Guidewire 70 passes through port 52 of connector 80 into guidewire hub 82. Connector 80 is configured to receive guidewire 70 at an angle of less than 45°. Connector 80 may be comprised of a polymer such as plastic, polycarbonate, polyvinyl chloride, or other suitable material. Guidewire 70 then advances through hub 82 into catheter 20. When completely inserted, guidewire 70 rests against the side of hub 82. The initial guidewire 70 length is selected such that when it is completely inserted, its proximal tip rests approximately a ¼ inch from the catheter's 20 proximal tip. This in turn provides additional protection from vein puncture or irritation from guidewire 70.

Guidewire 70 passes through wire sealed tube 50. Wire sealed tube 50 has a seal disposed therein such that it makes a watertight seal around guidewire 70. After guidewire 70 is placed through connector 80, it can slide its full length through the wire sealed tube 50, indentation 45, and the male swivel leur 40. Wire sealed tube 50 provides a slight resistance to the movement of guidewire 70. This resistance in wire sealed tube 50 prevents guidewire 70 from being moved too quickly through connector 80 and catheter 20 thereby in reducing a patient's discomfort by having a guidewire 70 move too quickly.

Port 62, used for flushing intravascular assembly 10, provides a means for connecting a syringe 85. Syringe 85 is connected to port 62 as shown in FIG. 4.

Syringe 85 is filled with flushing solution that may include saline, or other suitable solution. After syringe 85 is coupled to port 62, the flushing solution can be injected into the connector 80. It will be appreciated that syringe 85 will not inject the flushing fluid until a device such as a plunger to the syringe is depressed.

Flushing assembly 10 is generally recommended with an aqueous solution before, during, and after catheter insertion to assist in the movement of the catheter through the body and also to check for catheter patency. Additionally, the chances of clotting occurring in the patient are reduced when a catheter is flushed while moving through the body. Catheter 20 has been properly flushed before insertion into a patient's body when drops of flushing solution begin to emerge from catheter 20.

A user may then determine how long catheter 20 needs to be in order for the tip of the catheter to reach the desired location within a patient. The user may measure the distance between the insertion site and the desired tip location. If the necessary length for the catheter tip location is shorter than the length of the catheter 20, catheter 20 must be trimmed or cut to the correct length.

Guidewire 70 is then placed next to the body of the user and the user grips neck 64. Guidewire 70 is withdrawn through wire sealed tube 50 so that guidewire 70 is within the necessary length of catheter 20. Catheter 20 portion of assembly 10 may be trimmed using sterile scissors taking care to avoid cutting the guidewire 70. Note that approximately one half of an inch of catheter 20 should remain that has no guidewire within it. The resulting assembly 10 has a catheter 20 of proper length. Because guidewire 70 has been withdrawn from assembly 10, the guidewire handle will no longer rest against a user and a portion of the guidewire 70 will no longer be within the connector 80.

After trimming the catheter 20, but before installation, assembly 10 may be flushed again. Flushing prior to installation allows the user to recheck catheter patency and allows removal of any residue created during catheter 20 trimming.

It may be necessary to flush the catheter guidewire flushing apparatus 10 during insertion of the catheter. Flushing during installation can also assist in removing blood or other bodily fluids that may accumulate inside the lumen of assembly 10. Once installed in the patient, guidewire 70 can be left in assembly 10 in order to verify placement through radiographically. After verification, guidewire 70 is removed from assembly 10. In order to remove guidewire 70, guidewire's proximal end is pulled. If resistance is felt, assembly 10 should be flushed. The flushing solution lubricates the guidewire 70. Assembly 10 allows for flushing to take place without any guidewire 70 manipulation and at any time. Additionally, flushing may occur with a PICC assembly without having to reattach the syringe containing flushing solution.

Figure 5:
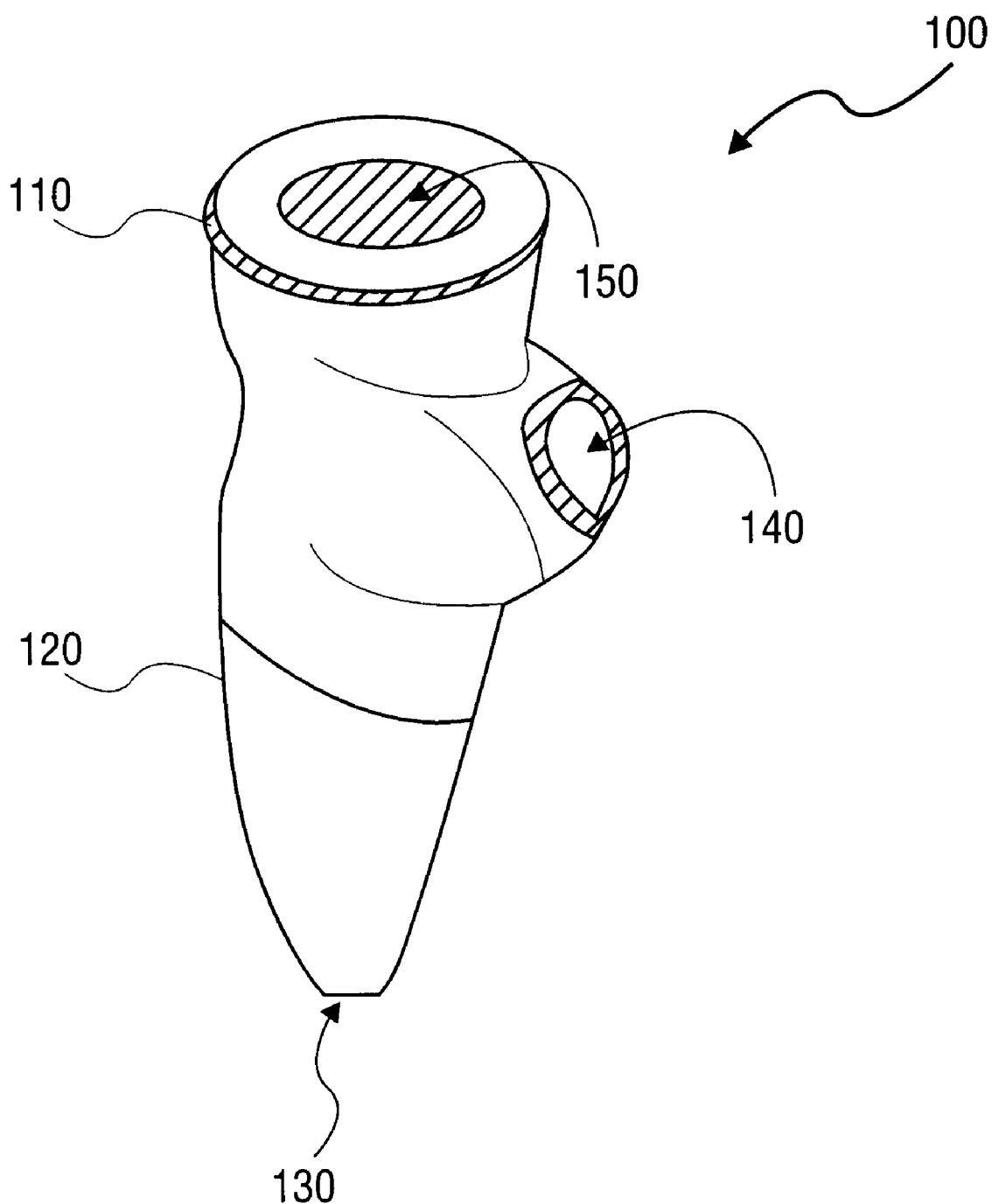
FIG. 5 is another embodiment of the invention wherein the hub has a guidewire port that protrudes from the hub.

FIG. 5 shows another embodiment of a connector used in an intravascular assembly. Connector 100 has an inlet port 150, a guidewire port 140, and an outlet port 130. Connector 100 has a wall 110 thickness of approximately 0.035 to 0.050 inches. The hub (not shown in FIG. 4) has an inner cavity that is substantially circular or elliptical in shape at the proximal portion of the connector 100 and the inner diameter of the hub narrows at the distal end of the hub. The inner diameter of inlet port 150, guide port 140, and outlet port 130 is 0.169 inches, 0.050 inches, 0.070 inches, respectively. While moving in the distal direction of connector 100, the lower portion of connector 100 begins to taper. Guidewire port 140 protrudes from the bottom portion of connector 100 approximately in the range of 0.10 to 0.15 inches. Guidewire port 140 slightly is also coupled to a syringe and operates in a similar fashion as that described above.

The ports described in connector 100 perform the same function as that which was described above. One of the advantages to a substantially spherical in shape connector is that it allows the intravascular assembly to move with greater ease when the patient moves and reduces the opportunity of connector 100 being caught in bedding or other like materials as that which happens with an L-shape or a Y-shape connector.

Connector 100 is coupled to a female leur lock 60 and to hub 82. Hub 82 is further coupled to PICC 25 which includes a catheter 20. It should be noted that connector 100 is secured to female leur lock 60 using conventional methods such as a snap fit or an adhesive. Furthermore, connector 100 is connected to hub 82 by hub 82 fitting securely within the inner diameter of connector 100. Conventional methods are used to attach hub 82 with connector 100.

In the preceding detailed description, the invention is described with reference to specific embodiments thereof. It will, however, be evident that various modifications and changes may be made thereto without departing from the broader spirit and scope of the invention as set forth in the claims. The specification and drawings are, accordingly, to be regarded in an illustrative rather than a restrictive sense.

What is claimed is:

1. A method of installing a catheter in a patient comprising:

attaching a connector without a L-configuration or a Y-configuration to a catheter, the connector having a first port located at a proximal end of the connector, a second port located at a middle portion of the connector, and a third port located at a distal end of the connector;

filling a syringe with a flushing solution;

injecting an amount of the flushing solution into the catheter, thereby flushing the catheter;

cutting a portion of the catheter so that only a desired length remains;

inserting a guidewire into the second port;

advancing the catheter into a patient by use of the guidewire; and withdrawing the guidewire from the catheter and the hub.

2. The method of claim 1, further comprising:

coupling a syringe to the first port.

3. An assembly comprising:

a hub having a proximal end and a distal end;

a catheter coupled to the distal end of the hub;

a connector coupled to the proximal end of the hub, the connector not having a Y-configuration or an L-configuration, the connector having a proximal end and a distal end and including a first port located at the proximal end of the connector, a second port located within a middle portion of the connector, and a third port located at the distal end of the connector; and a guidewire disposed through the second port.

4. The intravascular assembly of claim 3, wherein the connector is substantially cylindrical in shape.

5. The intravascular assembly of claim 3, wherein the connector has a substantially cylindrical body and the second port is flush with the cylindrical body.

6. The intravascular assembly of claim 5, wherein the second port is an in-line port.

7. The intravascular assembly of claim 3, further comprising:

a member lock coupled to a neck portion of the hub.

8. The intravascular assembly of claim 3, wherein the second port is adapted to receive the guidewire at about a 10° to 45° angle to the catheter.

9. An assembly comprising:

a hub having a proximal end and a distal end;

a catheter coupled to the distal end of the hub;

a connector coupled to the proximal end of the hub, the connector not having a Y-shaped or an L-shaped configuration, and the connector having a first port located at a proximal end of the connector, a second port located within a middle portion of the connector having a guidewire disposed therethrough, and wherein the guidewire is directed through a channel toward a third port located at a distal end of the connector;

a locking mechanism coupled to the first port to secure a syringe.

10. The intravascular assembly of claim 9, wherein the catheter is removably coupled to the outer surface of the distal end of the hub.

11. The intravascular assembly of claim 9, further comprising:

a watertight seal between the second port and third port to slidably dispose a guidewire therethrough.

12. The intravascular assembly of claim 9, further comprising:

a syringe coupled to the first port.

* * * * *